United States Patent
Cao et al.

(10) Patent No.: US 8,255,035 B2
(45) Date of Patent: Aug. 28, 2012

(54) COATED HYPODERMIC NEEDLE

(75) Inventors: Hong Cao, Savage, MN (US); Saurav Paul, Minnetonka, MN (US); Chou Thao, Brooklyn Park, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 926 days.

(21) Appl. No.: 11/967,518

(22) Filed: Dec. 31, 2007

(65) Prior Publication Data
US 2009/0171304 A1    Jul. 2, 2009

(51) Int. Cl.
A61B 5/042    (2006.01)
(52) U.S. Cl. .......... 600/374; 600/377; 600/509
(58) Field of Classification Search .......... 600/372, 600/486, 509, 373; 604/264, 272
See application file for complete search history.

(56) References Cited

U.S. PATENT DOCUMENTS

| | | | |
|---|---|---|---|
| 3,313,293 A * | 4/1967 | Chesebrough et al. ....... 600/373 |
| 3,682,162 A * | 8/1972 | Colyer ........................ 600/373 |
| 4,483,338 A * | 11/1984 | Bloom et al. .................. 606/50 |
| 5,078,714 A * | 1/1992 | Katims ........................ 606/38 |
| 5,403,311 A | 4/1995 | Abele et al. |
| 5,405,376 A | 4/1995 | Mulier et al. |
| 5,431,649 A | 7/1995 | Mulier et al. |
| 5,609,151 A | 3/1997 | Mulier et al. |
| 5,656,029 A * | 8/1997 | Imran et al. ................ 604/95.04 |
| 5,725,524 A | 3/1998 | Mulier et al. |
| 5,807,395 A | 9/1998 | Mulier et al. |
| 5,928,159 A * | 7/1999 | Eggers et al. ................. 600/547 |
| 5,976,110 A | 11/1999 | Greengrass et al. |
| 6,002,956 A * | 12/1999 | Schaer ........................ 600/381 |
| 6,298,256 B1 * | 10/2001 | Meyer ........................ 600/373 |
| 2002/0169371 A1 * | 11/2002 | Gilderdale .................. 600/373 |
| 2004/0193152 A1 * | 9/2004 | Sutton et al. .................. 606/48 |
| 2004/0260241 A1 * | 12/2004 | Yamamoto et al. .......... 604/117 |
| 2005/0267467 A1 | 12/2005 | Paul et al. |
| 2007/0005053 A1 | 1/2007 | Dando |

OTHER PUBLICATIONS www.wikipedia.org/wiki/Tuohy_needle.

* cited by examiner

Primary Examiner — Lee S Cohen
Assistant Examiner — Erin M Cardinal
(74) Attorney, Agent, or Firm — Dykema Gossett PLLC (57) ABSTRACT

A needle for a medical procedure includes a shaft with an inner surface, an outer surface, a proximal section, and a distal section. The distal section has a conductive tip configured to be a first electrode for voltage measurement. The needle further includes a first electrically insulative outer layer over a portion of the outer surface of the shaft. The conductive tip is adapted for insertion through tissue into, for example, a pericardial space of a patient. A system for determining the location of a needle during a medical procedure includes the needle and an anatomical mapping and localization system electrically coupled to the needle and adapted to measure voltage at the conductive tip. A system for determining tissue thickness during a medical procedure includes the needle, an anatomical mapping and localization system electrically coupled to the needle, and an electrocardiograph operatively coupled to the needle and adapted to monitor electrical activity at the conductive tip and at the second electrode. The needle may include a second electrode.

18 Claims, 6 Drawing Sheets

FIG.1

(PRIOR ART)

COATED HYPODERMIC NEEDLE

BACKGROUND OF THE INVENTION a. Field of the Invention

The instant invention is directed toward a needle and a system suitable for use in a medical procedure. The instant invention includes a needle where an electrically insulative outer layer is disposed over a portion of an outer surface of the needle, and a distal section of the needle is exposed to allow for mapping of the needle during a medical procedure.

b. Background Art

In an electrophysiology (EP) procedure, electrode catheters may be guided into the chambers of the heart and to strategic places along the heart's conduction system. The electrodes may then be used to record the electrical impulses of the heart and may define the location of abnormal electrical activity. EP procedures may be used to diagnose and treat ventricular tachycardia (VT) or atrial fibrillation (Afib) ablation, for example. One EP procedure is catheter ablation in which a catheter is inserted through the vasculature and into the heart, and energy is delivered through the catheter to that portion of the heart muscle that has been identified as causing an abnormal heart rhythm in order to ablate the tissue (e.g., to disconnect the pathway that is producing the abnormal rhythm).

Catheter ablation may be achieved epicardially without an incision into the chest cavity. In one technique for achieving percutaneous access into the pericardium (i.e., the membranous sac enclosing the heart), a hypodermic needle may be inserted into the chest cavity. The needle may be designed to facilitate entry into the space separating the pericardium and the heart surface (i.e., lift the pericardial sac). This procedure to access the pericardial space may eliminate the need to navigate tortuous vessels or fragile valves and may reduce risk of clot formation. The epicardium is the inner serous layer of the pericardium, lying directly upon the heart.

The needle may be inserted through tissue at the subxiphoid region and advanced toward the right ventricular apex. As the needle approaches the heart under fluoroscopic guidance, small amounts of contrast media (e.g., fluoroscope dye) are injected to document penetration of the needle tip into the pericardial space. Positioning of the needle is associated with layering of the contrast in the pericardial space. The needle tip may be advanced within a few centimeters from a cardiac silhouette (e.g., as seen on fluoroscopy) and then positioned for puncture of the pericardium. Fluoroscopy may reveal a V-shaped indentation (e.g., tenting) of the pericardium with contrast media injection just prior to pericardial puncture, and with puncture the contrast media may highlight the pericardium. The contrast media may be used to confirm the location of the needle by providing a particular "splash" configuration.

The use of fluoroscopy for achieving pericardial access has several potential limitations. Fluoroscopy provides only a two-dimensional image. Furthermore, fluoroscopy does not provide a clear image. In addition, the use of contrast in connection with fluoroscopy merely allows physicians to visualize a boundary for the heart and other tissue, rather than have direct visualization of the needle and the heart. Due to these limitations, epicardial procedures can be time consuming. Also, there remains a risk of puncturing a coronary artery or puncturing a heart chamber. In particular, there remains the risk of ventricular puncture (i.e., puncture in the ventricular wall) and bleeding (e.g., bleeding in the pericardial space).

Thus, there is a need for a system for mapping the location of a needle used for procedures, such as an epicardial procedure, including a needle configured for accurate mapping of the location of the needle tip.

BRIEF SUMMARY OF THE INVENTION

It is desirable to be able to map the location of a needle used for medical procedures, such as an epicardial procedure, in a manner that addresses, for example, the limitations associated with fluoroscopy.

A needle for a medical procedure includes a shaft with an inner surface, an outer surface, a proximal section, and a distal section. The distal section has a conductive tip configured to be a first electrode for voltage measurement. The needle further includes a first electrically insulative outer layer over a portion of the outer surface of the shaft. The conductive tip is adapted for insertion through tissue into a pericardial space of a patient.

A system for determining the location of a needle during a medical procedure includes a needle comprising a shaft with an inner surface, an outer surface, a proximal section, and a distal section. The distal section has a conductive tip configured to be a first electrode for voltage measurement. The needle further includes a first electrically insulative outer layer over a portion of the outer surface of the shaft. The system further includes an anatomical mapping and localization system electrically coupled to the needle and adapted to measure voltage at the conductive tip.

A system for determining tissue thickness during a medical procedure includes a needle comprising a shaft with an inner surface, an outer surface, a proximal section, and a distal section. The distal section has a conductive tip configured to be a first electrode for voltage measurement. The needle further includes a first electrically insulative outer layer over a portion of the outer surface of the shaft. The needle may include a second electrode disposed along the shaft. The system further includes an anatomical mapping and localization system electrically coupled to the needle and adapted to measure voltage at the conductive tip and an electrocardiograph operatively coupled to the needle and adapted to monitor electrical activity at the conductive tip.

The foregoing and other aspects, features, details, utilities, and advantages of the present invention will be apparent from reading the following description and claims, and from reviewing the accompanying drawings.

DETAILED DESCRIPTION OF THE INVENTION

During an epicardial procedure, the needle used to enter the pericardial space may be the same needle that is used to enter the epidural space when administering epidural anesthesia. The needle conventionally used for pericardial access is a Tuohy needle. A Tuohy needle may have a shaft that is generally curved for at least a portion of its length and defines a lumen. It may have a stylet within the lumen and may be blunt-tipped. The shaft may comprise stainless steel. For some embodiments, the shaft may be between about 89 and 125 mm in length and approximately 1.5 mm in outer diameter.

Figure 1:
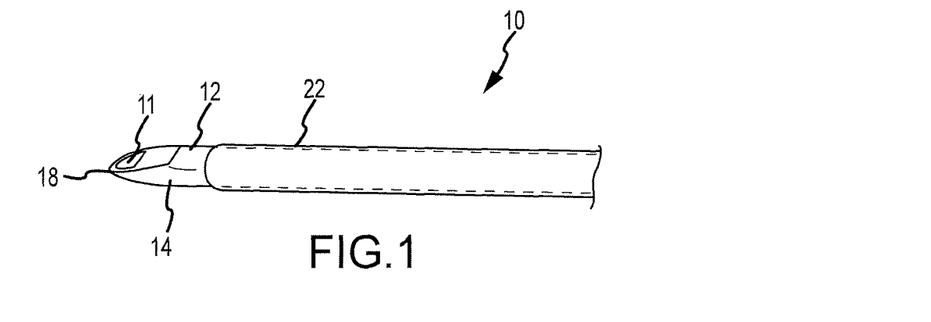
FIG. 1 is an isometric view of a first needle in accordance with the present teachings.

Referring now to FIG. 1, a first needle 10 in accordance with the present teachings may be similar to a Tuohy needle. The shaft of needle 10 may be hollow with an opening 11 at a distal end. The shaft of the needle may therefore define a lumen. A lumen may be provided because the needle 10 may be used to access the pericardial space, and various fluids (e.g., saline, contrast agents, and medicaments) or tools may be passed through the lumen of the needle 10 into the pericardial space. For example, a guidewire may be passed through the needle 10 into the pericardial space. After guidewire placement, the needle is withdrawn and exchanged for a standard introducer sheath. An ablation catheter may be introduced (e.g., passed over the guidewire through the introducer lumen) into the pericardial space. The catheter may then maneuver on the epicardial surface for diagnostic and therapeutic procedures.

Instead of using fluoroscopy to monitor the location of the needle for obtaining pericardial access, a three-dimensional mapping and localization system (e.g., the NavX™ system provided by St. Jude Medical) may be used to map various anatomical structures, including the heart, and the position of the needle used for obtaining pericardial access. The mapping and localization system may be configured to display, for example, the relative position of the needle with respect to a heart wall. The system may use a voltage measurement of the electrode (e.g., conductive needle) in the three-dimensional electrical field of the system.

Figure 2:
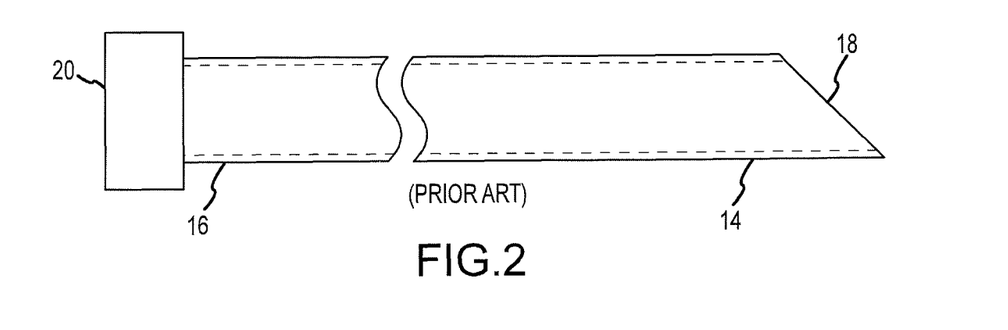
FIG. 2 is a view of a bare needle, showing an inner surface of the needle in phantom.

However, a bare needle shaft (e.g., as illustrated in FIG. 2) may distort the electrical signal by shorting the electrical field. The effect may cause needle location errors and may show the midpoint of the needle in the system's map (i.e., an average position of the whole needle shaft, rather than the tip). Accordingly, it is desired to have a needle that facilitates accurate localization of the needle tip in a localization and mapping system.

Figure 3:
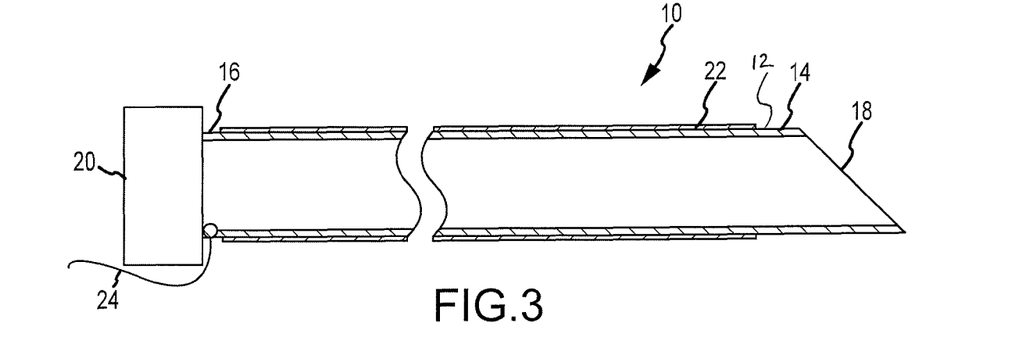
FIG. 3 is a cross-sectional view of the needle shown in FIG. 1.

Referring now to FIGS. 1 and 3, in the first needle 10 according to the present teachings, the needle 10 may comprise a shaft 12. The shaft 12 may have an inner surface and an outer surface. The shaft 12 may comprise a distal section 14 and a proximal section 16. The distal section 14 may have a conductive tip 18. The tip 18 may be configured to be a first electrode for voltage measurement. The proximal section 16 may be proximate to a hub 20. The hub 20 may comprise, for example, a rigid epidural needle connector. The hub 20 may be integral with the shaft 12 or may be a physically separate part which is attachable to the shaft 12.

The needle 10 may further comprise an outer layer 22. The outer layer 22 may be provided to yield more accurate mapping of the tip 18 of the needle 10 in three-dimensional anatomical mapping and localization systems to facilitate the puncture process and to reduce risk during pericardial access.

The layer 22 may be disposed over a portion of the outer surface of the shaft 12. A portion of the outer surface of the shaft 12 at the distal section 14 may be exposed. The tip 18 may be exposed in an embodiment. In an embodiment, approximately 1-4 mm of the distal section 14 may be exposed. A greater or smaller portion of the outer surface of the shaft 12 may be exposed and remain within the invention.

The layer 22 may comprise an electrically insulative material. In an embodiment, the layer 22 may comprise polymer tubing such as polytetrafluoroethylene (PTFE) heat shrink tubing. In this embodiment, the layer 22 may be about one ten thousandth (0.0001) of an inch in thickness. In another embodiment, the layer 22 may comprise a diamond-like carbon (DLC) coating. In this latter embodiment, the layer 22 may be approximately 3-5 microns in thickness. The layer 22 may be a generally thin layer to avoid compromising needle performance. The layer 22 may also comprise a dipped coating or a gas-vapor-deposited coating. The layer 22 may also be scratch-resistant and biocompatible in an embodiment.

The proximal section 16 of the shaft 12 may include a connector 24 (e.g., a lead wire) to connect (e.g., operatively couple) the needle 10 to a three-dimensional anatomical mapping and localization system. The connector 24 may be connected (e.g., securely attached) to the needle 10 in any manner conventional in the art (e.g., soldering, welding, and/or crimping). Because the shaft 12 is conductive, the connector 24 located at the proximal section 16 of the shaft 12 may connect (e.g., operatively couple) the exposed distal tip 18 of the needle 10 to the three-dimensional anatomical mapping and localization system. The insulated shaft 12 of the needle 10 may avoid distortion of the measurement voltage field of the three-dimensional anatomical mapping and localization system. The voltage may be measured at the exposed distal section 14 (e.g., tip 18) and may be mapped more accurately in the three-dimensional anatomical mapping and localization system as a point electrode. Generally, the accuracy of the three-dimensional anatomical mapping and localization system depends on the size of the electrode. A smaller electrode (e.g., the exposed tip 18 of the needle 10 serving as a point electrode) may provide increased accuracy over a larger electrode (e.g., an entire bare, conductive needle). During the EP procedure, the distal section 14 (e.g., tip 18) of the needle 10 may be located with the three-dimensional anatomical mapping and localization system as a point electrode. Physicians may therefore be able to judge the relative position of the distal section 14 (e.g., tip 18) of the needle 10 relative to ventricular or atrial structure based on the endocardial structure built into the EP procedure. Physicians may, therefore, avoid unintended ventricular puncture based on monitoring the proximity of the distal section 14 (e.g., tip 18) of the needle 10 to the endocardial surface.

Figure 4:
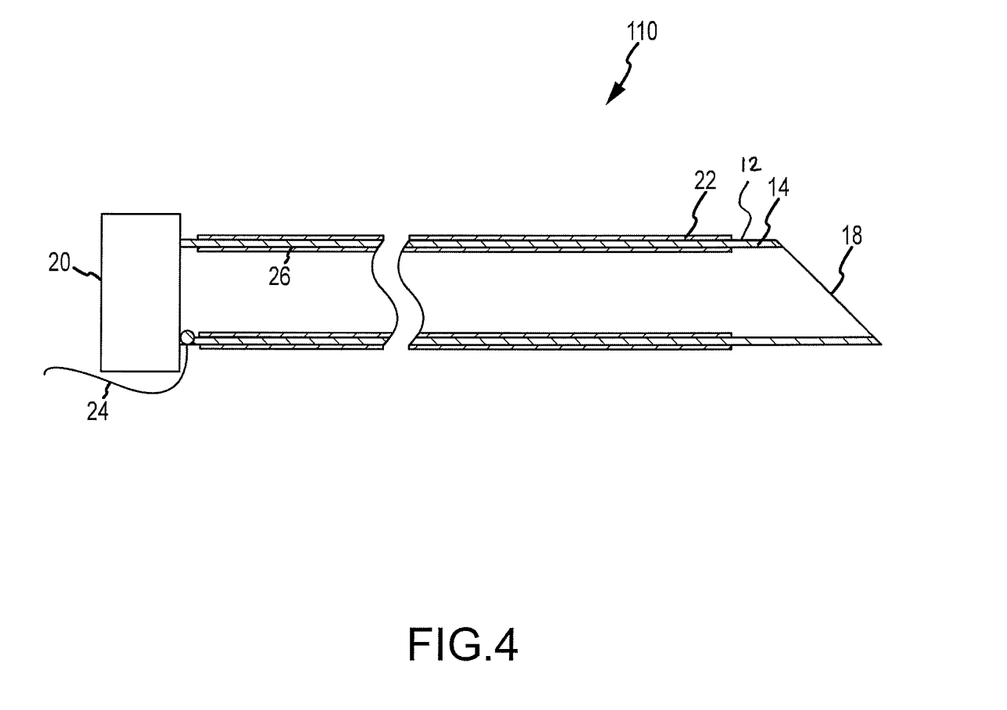
FIG. 4 is a cross-sectional view of a second needle in accordance with the present teachings.

Referring now to FIG. 4, in a second needle 110 according to the present teachings, the shaft 12 of the needle 110 may be substantially identical to the shaft 12 of the needle 10. However, the needle 110 may include an inner layer 26 disposed over a portion of the inner surface of the shaft 12. Accordingly, the needle 110 may include both the outer layer 22 disposed over a portion of the outer surface of the shaft 12 and the inner layer 26 disposed over a portion of the inner surface of the shaft 12. The layer 26 may comprise the same material and, for some embodiments, may be substantially the same thickness as the layer 22 described above. In some embodiments, the layer 26 may extend substantially the same length as the layer 22 described above. Alternatively, the material, thickness, and/or length of the layer 26 may be different from the thickness and/or length of the layer 22. Because the needles 10, 110 define a lumen, the inner surface (e.g., tube)

of the needle 10, 110 may have an effect on the electrical field and voltage measurement in three-dimensional anatomical mapping and localization systems. The layers 22 and 26 may provide better insulation and reduce the needle effect on the electrical field and voltage measurement in a three-dimensional anatomical mapping and localization system. A system for determining the location of a needle during a medical procedure may comprise the needle 10, 110 and an anatomical mapping and localization system electrically coupled to the needle 10, 110 and adapted to measure voltage at the conductive tip 18. The needles 10, 110 may also be used to monitor an electrocardiogram ("ECG") generated by an electrocardiograph. The ECG may include epicardial or endocardial contact through a localized catheter. In an embodiment, the needles 10, 110 may be used both to monitor ECG signals and to provide information with respect to a three-dimensional anatomical mapping and localization system. By using the needle 10, 110 to monitor ECG signals, physicians may obtain additional information, including confirmation that the needle has entered the pericardial sac, information regarding the thickness of the heart at the external surface (e.g., to know how long to ablate), electrical information for the heart, additional information relating to the anatomy of the heart, and information regarding the distance of the needle from the heart. Accordingly, a system for determining tissue thickness during a medical procedure may comprise the needle 10, 110, an anatomical mapping and localization system electrically coupled to the needle 10, 110 and adapted to measure voltage at the conductive tip 18, and an electrocardiograph operatively coupled to the needle 10, 110 and adapted to monitor electrical activity at the conductive tip 18.

Figure 5:
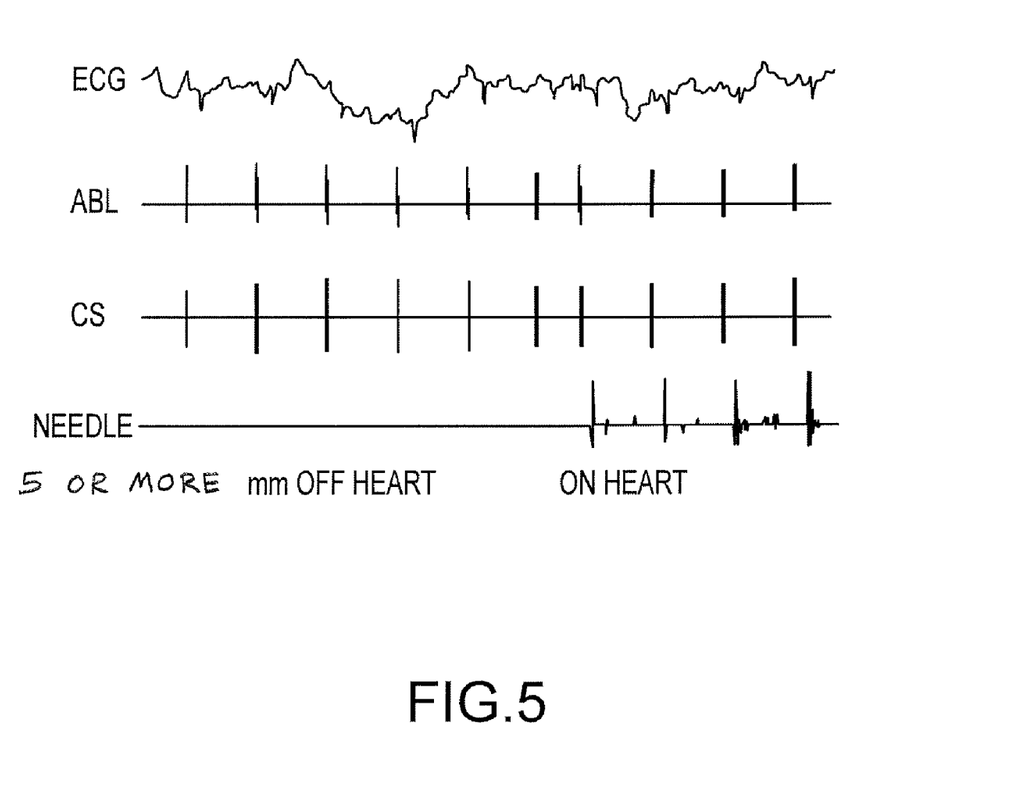
FIG. 5 is a chart showing a sample bipolar ECG recording from a needle in accordance with the present teachings.

Unipolar ECG does not change much during the puncture (see, e.g., the first trace in FIG. 5), but bipolar ECG changes dramatically and may be used as another proximity indicator to improve the safety of pericardial puncture. FIG. 5 illustrates a sample bipolar ECG recording from the needle 10, 110 when the needle is about 5 to 10 mm away from the heart and when needle is in contact with the heart (see, e.g., the lowest trace in FIG. 5). As evident in FIG. 5, the bipolar ECG recording may be used to convey information regarding the distance of the needle 10, 110 from the heart.

Figure 6:
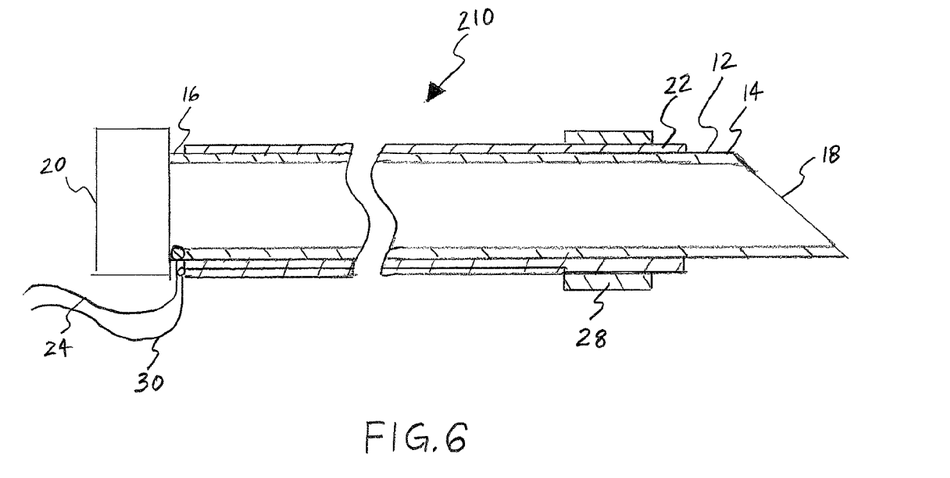
FIG. 6 is a cross-sectional view of a third needle in accordance with the present teachings.

Referring now to FIG. 6, in a third needle 210 according to the present teachings, the shaft 12 of the needle 210 may be substantially identical to the shaft 12 of the needle 10 or to the shaft 12 of the needle 110. The needle 210 may include only the outer layer 22 disposed over a portion of the outer surface of the shaft 12 (see needle 10 of FIGS. 1 and 3). Alternatively, the needle 210 may include both the outer layer 22 disposed over a portion of the outer surface of the shaft 12 and the inner layer 26 disposed over a portion of the inner surface of the shaft 12 (see needle 110 of FIG. 4). The needle 210 may further include a second electrode 28 for bipolar ECG monitoring and measurement. The second electrode 28 may be disposed along the shaft 12. The second electrode 28 may be separate from or external to the shaft 12 in an embodiment, whereas the first electrode may be the exposed distal section 14 of the shaft 12 in an embodiment. The second electrode 28 may be disposed externally of the layer 22 and may be approximately 1-4 mm (e.g., preferably 2 mm) away from the exposed distal section 14 of the shaft 12 in an embodiment. The second electrode 28 may generally comprise most conventional electrodes known in the art. For example, the second electrode 28 may comprise a regular 1 mm Pt/Ir electrode (i.e., Platinum/Iridium electrode). In another example, the electrode 28 may comprise stainless steel. The second electrode 28 may comprise a ring, mesh, fabric, or braid disposed around the needle 210. Although these types of electrodes are mentioned in detail, any form or shape of an electrode or any conductive material may be used for the electrode and remain within the invention.

A second connector 30 (e.g., a lead wire) may extend from the second electrode 28 for connection (e.g., operative coupling) to a three-dimensional anatomical mapping and localization system. The second connector 30 may be connected (e.g., securely attached) to the second electrode 28 in any manner conventional in the art. The outer layer 22 may define a lumen or recess (not shown) that extends proximally the length of the outer layer 22 (e.g., a longitudinally-extending recess or a longitudinally-extending annular channel). The lumen or recess may house the second connector 30 as it extends from the second electrode 28 toward the proximal section 16 of the shaft 12. The second connector 30 may further extend from near the proximal section 16 of the shaft 12 to a three-dimensional anatomical mapping and localization system. The use of the second electrode 30 may further allow physicians to more accurately determine the location of the distal section 14 (e.g., the tip 18) of the needle 210 relative to the various structures of the heart and facilitate the puncture process and reduce risks during pericardial access (e.g., puncture of the heart chamber).

The second electrode 28 and the exposed distal section 14 (e.g., the tip 18) of the needle 210 may form a bipolar pair. The second electrode 28 and the exposed distal section 14 (e.g., the tip 18) of the needle 210 may be mapped in a three-dimensional anatomical mapping and localization system separately so that the orientation of the needle 210 may be displayed. Bipolar ECG can be monitored from the two electrodes (e.g., the second electrode 28 and the point electrode at the exposed distal section 14 of the shaft 12) to improve the efficacy and safety of the puncture. Unlike unipolar ECG, the differential bipolar ECG minimizes the far field signal and represents the local electrical activity in the myocardium. During an EP procedure, physicians may use the bipolar ECG as a proximity indicator to help determine if the needle 210 is in contact with the heart and to thereby avoid unintended puncture through the heart wall. When the needle 210 is not in contact with or not close enough to (e.g., within several millimeters) the myocardium, the bipolar ECG associated with the needle is minimal (see, e.g., the lowest trace in FIG. 5) because there is no local cardiac activity. The bipolar signal increases significantly when the needle 210 contacts the heart (see, e.g., FIG. 5). During an EP procedure, physicians may be cautious to move the needle 210 forward when a high amplitude bipolar signal is observed. The bipolar ECG signal can further indicate the location of the needle 210 on the heart so that physicians can puncture at an appropriate location. With additional catheters in the heart, such as a CS catheter (i.e., coronary sinus catheter) or HIS catheter (i.e., HIS bundle catheter), physicians may determine the location of the needle 10 based on the relationship of the sensed ECG signals to the location of the additional catheters. Physicians can thereby select an appropriate location to puncture so that further procedures, including catheter deployment, may be safer and more efficient.

Figure 7:
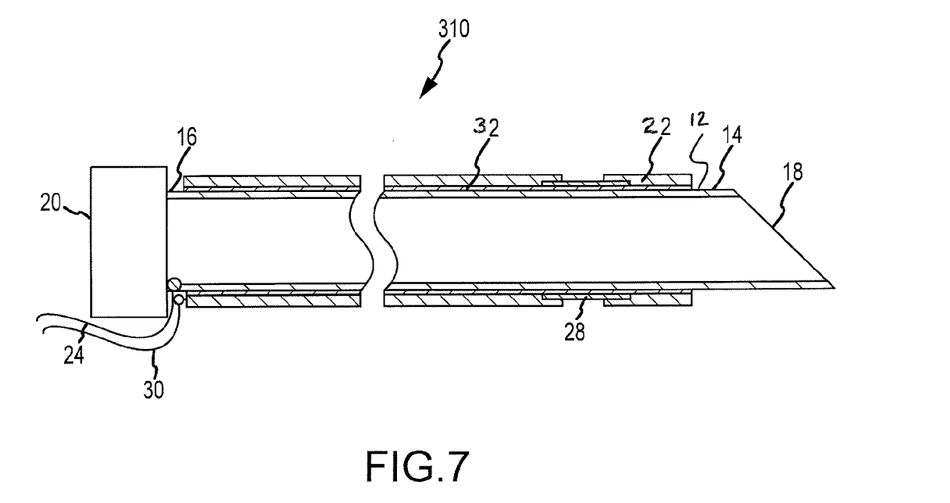
FIG. 7 is a cross-sectional view of a fourth needle in accordance with the present teachings.

Referring now to FIG. 7, in a fourth needle 310 according to the present teachings, the shaft 12 of the needle 310 may be substantially identical to the shaft 12 of the needle 210. However, the needle 310 may further comprise an intermediate layer 32. The outer layer 22 may be disposed over a portion of the outward-most surface of the intermediate layer 32. The outer layer 22 may also be disposed over a portion of the second electrode 28. Accordingly, in an embodiment, a portion of the second electrode 28 may be exposed, and a portion of the second electrode 28 may be covered by the outer layer 22. In this embodiment, the outer layer 22 may thereby help to fix the position of the electrode 28 on the shaft 12. The intermediate layer 32 may comprise the same material and, for some embodiments, may be substantially the same thickness as the outer layer 22 and/or the inner layer 26 described above. The intermediate layer 32 may extend substantially the same length as the outer layer 22 and/or the inner layer 26 described above. Alternatively, the material, thickness, and/or length of the intermediate layer 32 may be different from the material, thickness, and/or length of the outer layer 22 and/or the inner layer 26. The second connector 30 may be connected (e.g., securely attached) to the second electrode 28 in any manner conventional in the art. The outer layer 22 or the intermediate layer 32 may define a lumen or recess (not shown) that extends proximally the length of the outer layer 22 (e.g., a longitudinally-extending recess or a longitudinally-extending annular channel). This lumen may house the second connector 30 as it extends from the second electrode 28 toward the proximal section 16 of the shaft 12. The second connector 30 may further extend from near the proximal section 16 of the shaft 12 to a three-dimensional anatomical mapping and localization system.

Figure 8:
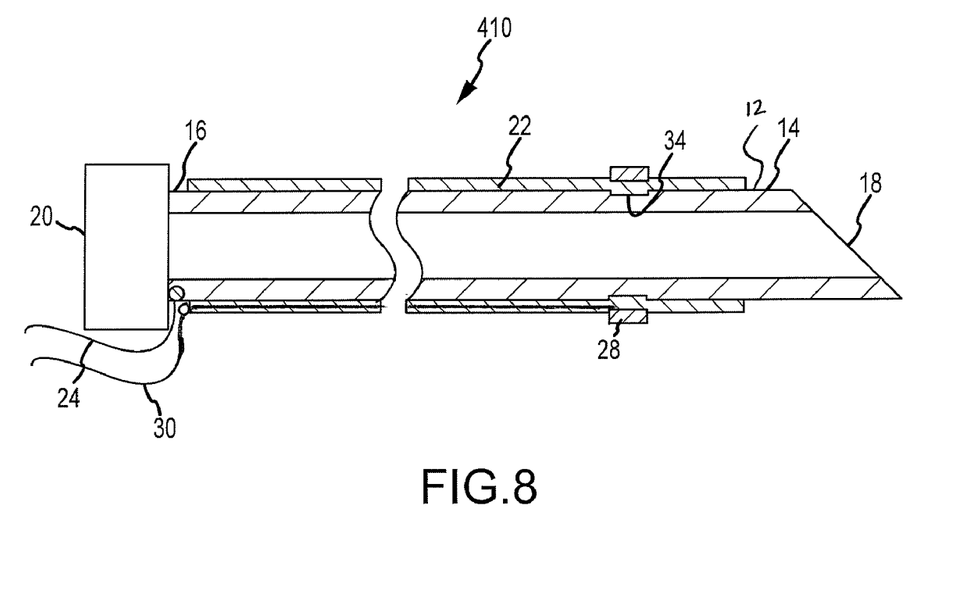
FIGS. 8-9 are cross-sectional views of a fifth needle in accordance with the present teachings.
Figure 9:
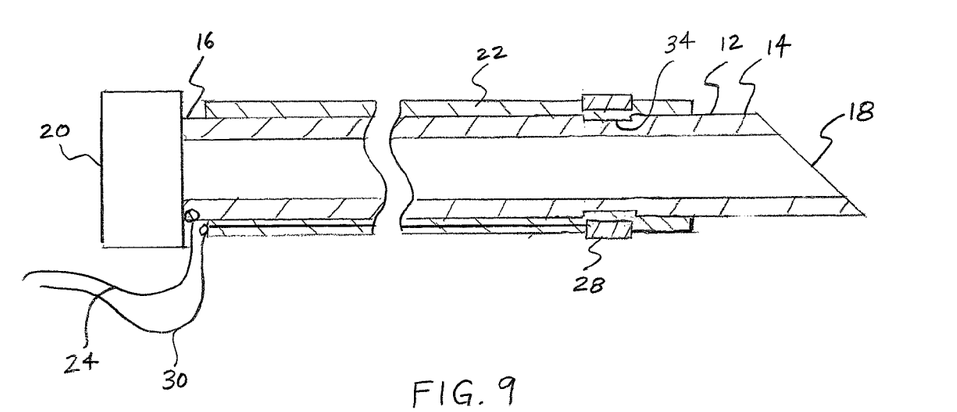

Referring now to FIG. 8, in a fifth needle 410 according to the present teachings, the shaft 12 of the needle 410 may be substantially identical to the shaft 12 of the needle 210. However, the needle 410 may further comprise a recess 34 on the outer surface of the shaft 12. The recess 34 may comprise an annular recess, and the recess 34 may be configured to receive the second electrode 28. As illustrated in FIG. 8, the second electrode 28 may be slightly embedded into the outer surface of the outer layer 22. Alternatively, the second electrode 28 may be embedded further into or fully through the outer layer 22 so as to partially or fully reside in the recess 34. As illustrated in FIG. 9, the recess 34 may provide for a smoother outer surface on the needle 410 after the second electrode 28 is disposed over the shaft 12 than the outer surface of the needle 410 as depicted in FIG. 8 since a greater portion of the second electrode 28 may be disposed in the recess 34 and only the remainder of the second electrode 28 may project above the outer layer 22. A smooth surface may facilitate puncture by the needle 410 during an EP procedure and may reduce the risk of adverse effects such as blood coagulation.

Figure 10:
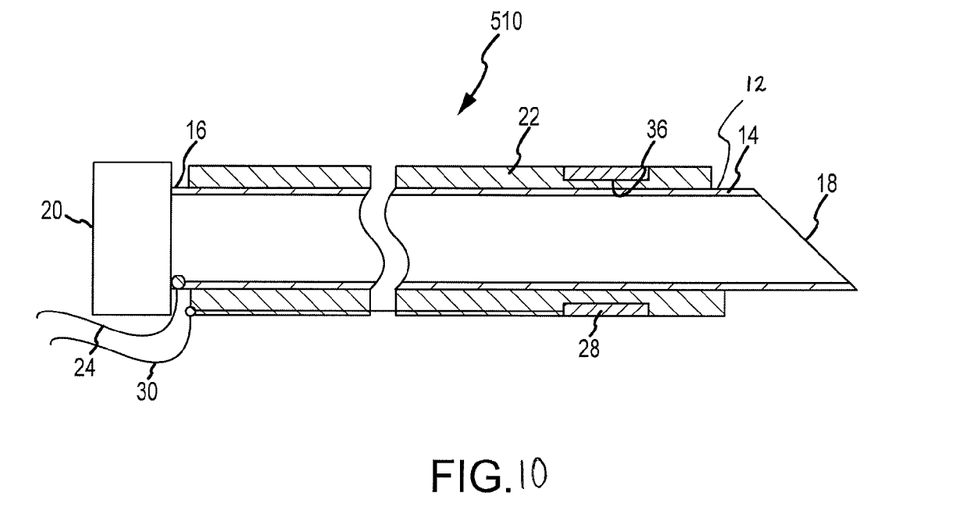
FIG. 10 is a cross-sectional view of a sixth needle in accordance with the present teachings.

Referring now to FIG. 10, in a sixth needle 510 according to the present teachings, the shaft 12 of the needle 510 may be substantially identical to the shaft 12 of the needle 210. However, the needle 510 may further comprise a recess 36 on the outer surface of the outer layer 22. The recess 36 may comprise an annular recess, and the recess 36 may be configured to receive the second electrode 28. When the second electrode 28 is mounted in the recess 36, the outer surface of the needle 510 may be even smoother than the outer surface of the needle 410 as depicted in FIG. 8 or 9. The recess 36 may be configured in size and shape so that when the recess 36 receives the second electrode 28, the outer surface of the second electrode 28 is substantially flush with the outer surface of the outer layer 22. A smooth surface may facilitate puncture by the needle 510 during an EP procedure and may reduce the risk of adverse effects such as blood coagulation.

Although one additional (i.e., second) electrode is mentioned in detail in the above teachings, fewer or more electrodes could be included on the needle 10, 110, 210, 310, 410, 510. For example, two or more separate electrodes could be attached to the needle 10, 110, 210, 310, 410, 510. Two separate electrodes would allow for monitoring multiple bipolar ECG signals, instead of one separate electrode and the exposed distal section 14 of the needle 10, 110, 210, 310, 410, 510 forming a single bipolar pair. More bipolar ECGs can be monitored by including more electrodes on the shaft 12 of the needle.

Although several embodiments have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the invention as defined in the appended claims.

What is claimed is:

1. A hollow needle assembly comprising:
a one-piece shaft body comprising an inner surface and an outer surface, wherein said shaft body is electrically conductive and wherein a distal-most section of said shaft body is exposed, thereby forming a circumferentially and axially extending annular portion having a first axial length and a tip configured to be a first electrode for voltage measurement, wherein a proximal-most section of said shaft body is configured for connection to an anatomical mapping and localization system;
a second electrode fixed in a position along said shaft body, said second electrode having a distal axial end surface and a proximal axial end surface, and said second electrode having a second axial length extending between the distal axial end surface and the proximal axial end surface of the second electrode;
an outer layer of electrically-insulative material that extends over said outer surface of said shaft body between said distal-most section and said proximal-most section of said shaft body, wherein said outer layer of electrically-insulative material does not extend over said exposed distal-most section of said shaft body, and wherein said tip is configured for insertion into tissue such that the entire first axial length of the circumferentially and axially extending annular portion and the entire second axial length of the second electrode are configured for insertion into the tissue; and
a wire extending from the second electrode to at least the proximal-most section of the shaft body.

2. The needle assembly in accordance with claim 1, wherein the outer layer comprises material selected from the group consisting of polytetrafluoroethylene and diamond-like carbon coating.

3. The needle assembly in accordance with claim 1, further comprising an inner layer of electrically-insulative material over a portion of said inner surface of said shaft body.

4. The needle assembly in accordance with claim 1, further comprising a connector disposed at said proximal-most section, said connector configured for electrically coupling said distal-most section of said shaft body to an anatomical mapping and localization system.

5. The needle assembly in accordance with claim 1, wherein said second electrode is disposed on an outer surface of the outer layer.

6. The needle assembly in accordance with claim 1, further comprising an intermediate layer of electrically-insulative material, wherein said outer layer is disposed on an outer surface of the intermediate layer, wherein the intermediate layer is separate from the outer layer.

7. The needle assembly in accordance with claim 6, wherein the outer layer at least partially covers the second electrode.

8. The needle assembly in accordance with claim 1, wherein said shaft body includes an annular recess, wherein said annular recess has substantially the same axial length as said second electrode and wherein said annular recess is axially aligned with said second electrode.

9. The needle assembly in accordance with claim 1, wherein said outer layer includes an annular recess configured to receive at least a portion of said second electrode, wherein said annular recess has a third axial length that is constant and that is substantially the same as the second axial length of the second electrode.

10. The needle assembly in accordance with claim 1, wherein an outer surface of said second electrode is substantially flush with an outer surface of the outer layer.

11. A needle assembly that facilitates localization during a medical procedure, the needle assembly comprising:
- a one-piece shaft body comprising an inner surface and an outer surface, wherein said shaft body is electrically conductive and wherein a distal-most section of said shaft body is exposed, thereby forming a circumferentially and axially extending annular portion having a first axial length and a tip configured to be a first electrode for voltage measurement, and wherein a proximal-most section of said shaft body is configured for connection to an anatomical mapping and localization system;
- a second electrode fixed in a position along said shaft body, said second electrode having a distal axial end surface and a proximal axial end surface, and said second electrode having a second axial length extending between the distal axial end surface and the proximal axial end surface of the second electrode;
- an outer layer of electrically-insulative material extending over said outer surface of said shaft body between said distal-most section and said proximal-most section of said shaft body, wherein said outer layer of electrically-insulative material does not extend over said exposed distal-most section of said shaft body, and wherein said tip is configured for insertion into tissue such that the entire first axial length of the circumferentially and axially extending annular portion and the entire second axial length of the second electrode are configured for insertion into the tissue;
- a first wire connected to the proximal-most section of said shaft body and adapted to deliver electrical signals to the anatomical mapping and localization system, which is adapted to measure voltage at said tip; and
- a second wire extending from the second electrode to at least the proximal-most section of the shaft body and adapted to deliver electrical signals to the anatomical mapping and localization system.

12. The needle assembly according to claim 11, further comprising an inner layer of electrically-insulative material extending over a portion of said inner surface of said shaft body.

13. The needle assembly according to claim 11, further comprising an intermediate layer of electrically-insulative material, wherein said outer layer is disposed on an outer surface of the intermediate layer, wherein the intermediate layer is separate from the outer layer.

14. The needle assembly according to claim 13, wherein the outer layer at least partially covers the second electrode.

15. The needle assembly according to claim 11, wherein said shaft body includes an annular recess, wherein said annular recess has substantially the same axial length as said second electrode and wherein said annular recess is axially aligned with said second electrode.

16. The needle assembly according to claim 11, wherein an outer surface of said second electrode is substantially flush with an outer surface of the outer layer.

17. The needle assembly in accordance with claim 11, wherein said shaft body includes an annular recess, wherein said annular recess has the same axial length as said second electrode and wherein said annular recess is axially aligned with said second electrode.

18. The needle assembly in accordance with claim 11, wherein the shaft body is configured to be operatively coupled to an electrocardiograph adapted to monitor electrical activity at said conductive tip of said shaft body.

\* \* \* \* \*